United States Patent [19]

Laballery

[11] Patent Number: 5,078,151
[45] Date of Patent: Jan. 7, 1992

[54] MEDICAL AUSCULTATION DEVICE

[76] Inventor: Vincent Laballery, 20 Rue du Moulin, 92800 Putneau, France, 92800

[21] Appl. No.: 571,556

[22] PCT Filed: Mar. 3, 1989

[86] PCT No.: PCT/FR89/00089
§ 371 Date: Sep. 4, 1990
§ 102(e) Date: Sep. 4, 1990

[87] PCT Pub. No.: WO89/07908
PCT Pub. Date: Sep. 8, 1989

[30] Foreign Application Priority Data

Mar. 4, 1988 [FR] France ............... 88 02773

[51] Int. Cl.⁵ .............................................. A61B 7/02
[52] U.S. Cl. ..................................... 128/715; 128/773
[58] Field of Search ................. 128/715, 672, 773

[56] References Cited

FOREIGN PATENT DOCUMENTS

| | | |
|---|---|---|
| 0179971 | 3/1989 | European Pat. Off. . |
| 2161268 | 6/1973 | Fed. Rep. of Germany . |
| 618598 | 8/1980 | Switzerland . |
| 0672412 | 11/1989 | Switzerland .............. 128/715 |

*Primary Examiner*—William E. Kamm
*Assistant Examiner*—Scott M. Getzow
*Attorney, Agent, or Firm*—Hoffman, Wasson & Gitler

[57] ABSTRACT

A medical auscultation device comprising an element intended to be applied to a patient's skin, which is characterized by the fact that it comprises on or in the vicinity of this element a heating resistance which is supplied by a contactor from an electric current source such as a battery.

13 Claims, 1 Drawing Sheet

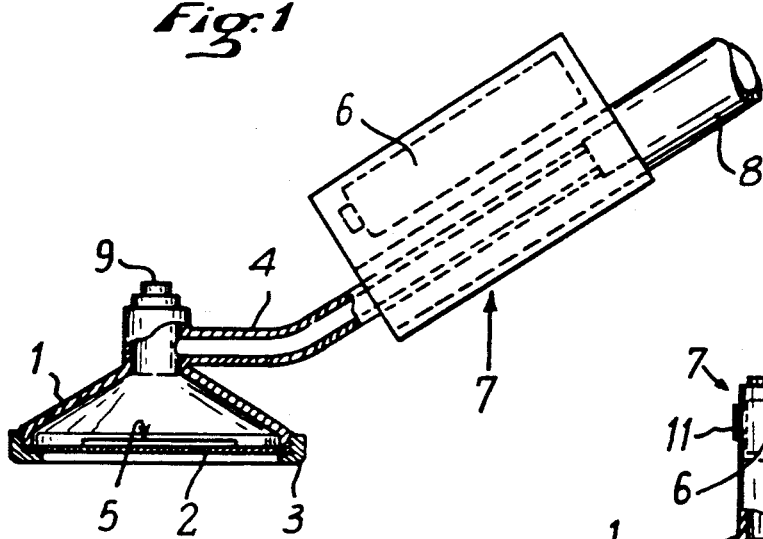
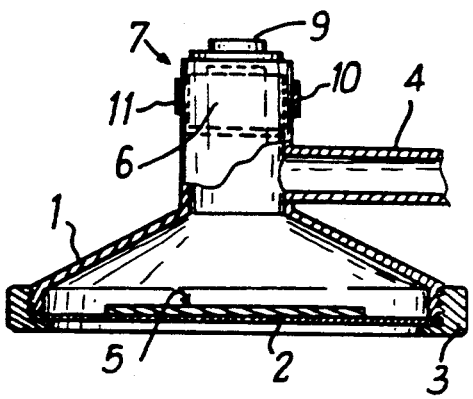
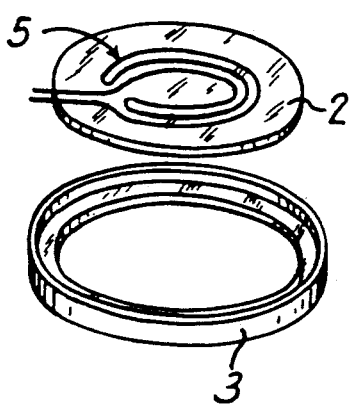
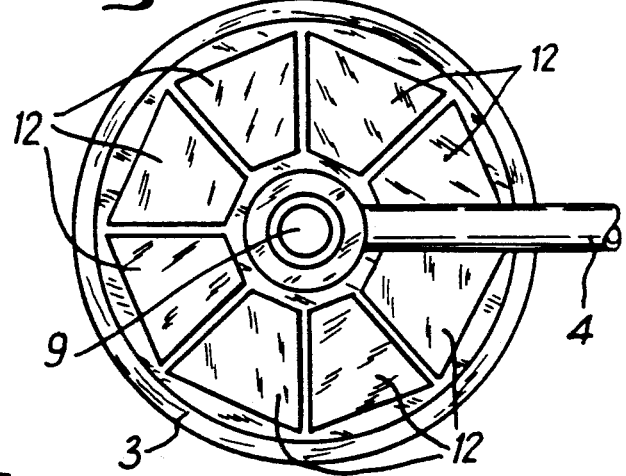
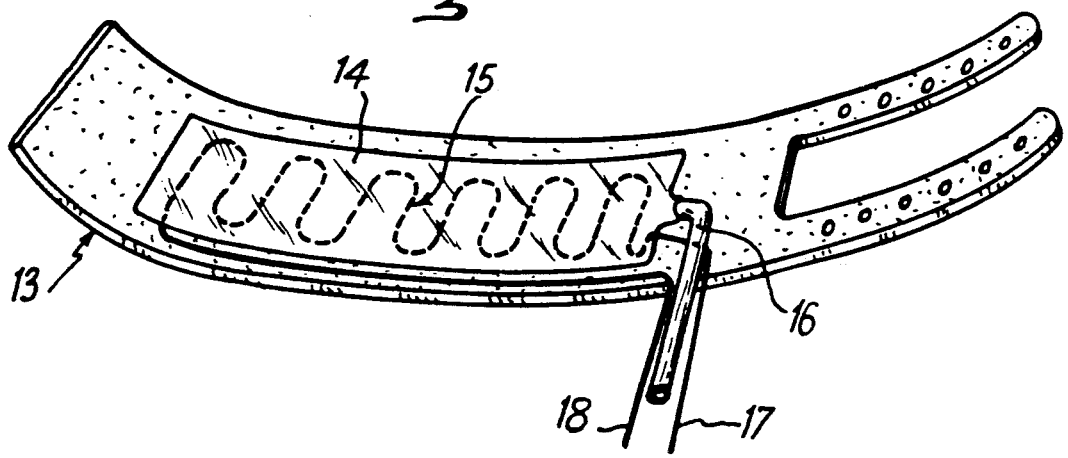

MEDICAL AUSCULTATION DEVICE

This invention has as its object an improved auscultation device.

Medical auscultation devices such as stethoscopes or sphygmomanometers which require the application to the patient's skin of an element intended to pick up a noise or a pressure are already known.

These known devices present the drawback that the first contact of the measuring element with the skin causes a sensation of cold and causes reactions from the patient, which are able to disturb the examination that it is desired to make.

This is the case in particular when it is desired to measure a parameter of the blood circulation, because a sudden sensation of cold often causes a modification of the cardiac rhythm.

Also, this sensation of cold often makes babies or young children that are to be examined scream or cry.

This invention aims at producing medical auscultation devices which prevent this drawback while being of a simple and not very costly embodiment.

This invention has as its object a medical auscultation device comprising an element intended to be applied to the patient's skin, which is characterized by the fact that it comprises on or in the vicinity of this element a heating resistance which is supplied by a contactor from an electric current source such as a battery, a light and portable device.

In a first embodiment, the invention is a stethoscope in which the electrical resistance is applied to the membrane, preferably to the face of the latter which is not in contact with the patient's skin.

The electrical resistance can consist of a filament which is glued along a winding passage to the face of the membrane.

It can also be directly made on the membrane thanks to the known technique of printed circuits.

In a particular embodiment, the resistance of the membrane is supplied with electric current by a battery placed in a case attached to the tube which connects the body of the stethoscope to the ear tips, preferably in the vicinity of the body of the stethoscope.

In another embodiment of the invention, the resistance is supplied by a small-sized battery, which is located in a case on the top of the body of the stethoscope and which can be recharged thanks to electric contacts located on the periphery of the case of the battery.

According to yet another embodiment of the invention, the electrical energy is provided to the resistance by a small-sized battery, placed in a case located on the top of the body of the stethoscope, which is supplied by multiple photovoltaic cells which are placed on the upper face of the cup of the stethoscope and which assure the automatic recharging of the battery.

According to these various embodiments, a slight heating of the membrane of the stethoscope is caused by supplying it with electric current by a switch consisting, for example, of a push button that it suffices to press for a very short time, just before the moment when the cup of the stethoscope is applied to the patient's skin.

In a second embodiment, the invention is applied to a sphygmomanometer and is characterized by the fact that the inflatable rubber pocket, which is applied to the patient's skin and inside of which pressurized air is sent to measure the arterial pressure, comprises a resistance in the vicinity of its face which is applied against the patient's skin, this resistance being supplied with electric current by a switch to heat the rubber before its application to the patient's skin.

To make the invention better understood, several embodiments taken as examples and shown in the accompanying drawing will now be described by way of illustration and without any limiting nature.

In this drawing:

FIG. 1 is a view in partial section of a stethoscope according to a first embodiment of the invention, FIG. 2 is a perspective view showing the membrane of the stethoscope of FIG. 1 as well as its attachment ring, FIG. 3 is a view in partial section of a stethoscope according to a second embodiment of the invention, FIG. 4 is a top view of a stethoscope according to a third embodiment of the invention, and FIG. 5 is a diagrammatic perspective view showing a sphygmomanometer according to the invention.

A first embodiment of the invention has been diagrammatically shown in FIG. 1, in partial section.

In this figure is seen cup 1 of the stethoscope which is provided with a membrane 2 attached, for example, by a screw mounting ring 3 or by a clip. A tube 4 corresponds, on the one hand, to its lower end with the inside of the cup, and, on the other hand, to its other end with ear tips, not shown.

According to the invention, a resistance 5 is glued to the inside face of membrane 2.

This resistance is supplied with electric current by one or more batteries 6 placed in a case 7 attached to rubber tube 8 which extends tube 4 in the direction of the ear tips.

Battery or batteries 6 are connected electrically to resistance 5 by a push-button switch 9 which is placed on the upper part of the body of the cup.

For reasons of simplicity of the drawing, the electric connections connecting resistance 5 to battery 6 by push-button switch 9 have not been shown in the drawing, but it is sufficient to known that these elements are connected in series to be able usefully to make these connections.

In FIG. 2 are found membrane 2, mounting ring 3 as well as resistance 5, which, in the embodiment described, consists of a wire glued to the upper face of membrane 2.

This resistance wire 5 can be placed along a different passage, for example with its ends diametrically opposite.

In a variant, resistance 5 can be made on membrane 2 by the conventional technique of printed circuits.

In the embodiment of FIG. 3, cup 1 is found provided with its membrane 2 which supports resistance 5 and which is attached to the cup by screw ring 3, the sound waves being transmitted by tubing 4 to the ear tips, not shown.

In this embodiment, the supply in electricity is performed from a small-sized battery 6 which is connected to resistance 5 by push button 9 attached to case 7 of battery 6.

In this embodiment, two contacts 10 and 11, placed on the outer surface of case 7 of battery 6, make it possible to recharge the latter when this is necessary, with an auxiliary current source, as is standard for this type of small batteries.

In the embodiment of FIG. 4, the same structure is found as in that of FIG. 3, except battery 6 is constantly recharged thanks to photovoltaic elements 12, which are placed on the upper face of cup 1 and which, when they are subjected to the effects of the light, send current into battery 6.

FIG. 5 is a diagrammatic perspective view of a sphygmomanometer according to the invention.

This sphygmomanometer comprises a cuff 13 as is standard, as well as a rubber pocket 14 inside of which a variable air pressure can be made to prevail thanks to tubing 16 which is connected to a pump.

According to the invention, the face of pocket 14, which is in contact with the patient's skin, is provided with a resistance 15 which in this case consists of a wire arranged in a coil, and which, by two conductors 17 and 18, is supplied with electric current to be able to heat the wall of pocket 14.

The resistance can be incorporated in the membrane and the heating can be self-regulated.

As in the preceding cases, a switch, not shown, makes it possible to assure the heating of the outer wall of pocket 14 slightly before the application of the cuff to the patient.

According to the invention, it is possible to produce a medical auscultation device which is of a simple and economical embodiment and which makes it possible to prevent causing, on the part of the patient, reactions which disturb the examination when an element that is not at body temperature is applied to the patient's skin.

It is well understood that the embodiments which have been described above exhibit no limiting nature and that they can receive any modifications desired without going outside the scope of the invention.

I claim:

1. A medical auscultation device comprising:
   a) an element for application to a patient's skin;
   b) an electric current source;
   c) a contactor
   d) a heating resistance supplied by said contactor from said electric current source connected to said element.

2. A medical auscultation device as claimed in claim 1, wherein said electric current source is a battery.

3. A medical auscultation device as claimed in claim 2, wherein said device is a stethoscope having a membrane for contact with a patient's skin with a patient contact side and a patient non-contact side and wherein said heating resistance is applied to said patient non-contact side of said membrane.

4. A medical auscultation device as claimed in claim 3, wherein said heating resistance consists of a filament which is adhered along a winding passage to the face of said patient non-contact side of said membrane.

5. A medical auscultation device as claimed in claim 3, wherein said heating resistance is printed on to said membrane.

6. A medical auscultation device as claimed in claim 3, further comprising a tube having first and second ends, wherein said first end is connected to said element of said stethoscope; ear tips connected to said second end of said tube; and a case attached to said tube for holding said battery in the vicinity of said element.

7. A medical auscultation device as claimed in claim 3, further comprising a tube having first and second ends, wherein said first end is connected to said element of said stethoscope; ear tips connected to said second end of said tube; and a case placed directly upon said element for holding said battery in the vicinity of said element.

8. A medical auscultation device as claimed in claim 7, wherein said case further comprises contacts located on the periphery of said case for recharging said battery contained therein.

9. A medical auscultation device as claimed in claim 7, wherein said element further comprises at least one photovoltaic cell thereon for recharging said battery.

10. A medical auscultation device as claimed in claim 1, further comprising a switch means for operating said heating resistance, which consists of a push button.

11. A medical auscultation device as claimed in claim 1, wherein said heating resistance is incorporated into said membrane.

12. A medical auscultation device as claimed in claim 1, wherein said heating resistance is self-regulated.

13. A medical auscultation device as claimed in claim 1, wherein said device is a sphygmomanometer having an inflatable rubber face which is applied to a patient's skin and a heating resistance applied to said face, supplied with electrical current by a switch means.

* * * * *

UNITED STATES PATENT AND TRADEMARK OFFICE
CERTIFICATE OF CORRECTION

PATENT NO. : 5,078,151

DATED : January 7, 1992

INVENTOR(S) : Vincent Laballery

It is certified that error appears in the above-identified patent and that said Letters Patent is hereby corrected as shown below:

On the Title page:

line 76, the inventor's address should properly read:

--20 Rue du Moulin, 92800 Puteaux, France--

Signed and Sealed this

Twenty-seventh Day of April, 1993

Attest:

*Attesting Officer*

MICHAEL K. KIRK

*Acting Commissioner of Patents and Trademarks*